United States Patent
Roberts et al.

(10) Patent No.: US 9,526,845 B2
(45) Date of Patent: Dec. 27, 2016

(54) SAFETY DEVICE FOR A PRE-FILLED SYRINGE AND INJECTION DEVICE

(75) Inventors: Gareth Roberts, Wrexham (GB); Sioned Owen, Denbigh (GB); Matthew Ekman, Macclesfield (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/807,046

(22) PCT Filed: Jun. 21, 2011

(86) PCT No.: PCT/EP2011/060324
§ 371 (c)(1),
(2), (4) Date: Apr. 29, 2013

(87) PCT Pub. No.: WO2012/000839
PCT Pub. Date: Jan. 5, 2012

(65) Prior Publication Data
US 2013/0211339 A1   Aug. 15, 2013

(30) Foreign Application Priority Data
Jul. 2, 2010  (EP) ................................. 10168324

(51) Int. Cl.
A61M 5/32   (2006.01)

(52) U.S. Cl.
CPC ........... *A61M 5/3202* (2013.01); *A61M 5/326* (2013.01); *A61M 5/3271* (2013.01); *A61M 2005/3267* (2013.01)

(58) Field of Classification Search
USPC ....... 600/573, 579, 576, 110, 192, 195, 197, 600/198, 31, 813
See application file for complete search history.

(56) References Cited

U.S. PATENT DOCUMENTS

| | | | | |
|---|---|---|---|---|
| 4,160,450 A | * | 7/1979 | Doherty | 604/164.08 |
| 4,863,434 A | * | 9/1989 | Bayless | 604/198 |
| 4,871,355 A | | 10/1989 | Kikkawa | |
| 4,968,299 A | * | 11/1990 | Ahlstrand et al. | 604/90 |
| 5,026,353 A | * | 6/1991 | Bartman | 604/192 |
| 5,167,640 A | * | 12/1992 | Balding | 604/192 |
| 5,176,656 A | * | 1/1993 | Bayless | 604/198 |
| 5,300,030 A | * | 4/1994 | Crossman et al. | 604/136 |
| 5,304,151 A | * | 4/1994 | Kuracina | 604/198 |
| 5,320,603 A | * | 6/1994 | Vetter et al. | 604/82 |
| 5,368,568 A | * | 11/1994 | Pitts et al. | 604/110 |

(Continued)

FOREIGN PATENT DOCUMENTS

| | | |
|---|---|---|
| EP | 1321158 | 6/2003 |
| WO | WO 2007/047200 | 4/2007 |

OTHER PUBLICATIONS

International Search Report for Int. App. No. PCT/EP2011/060234, completed Jan. 31, 2012.

*Primary Examiner* — Scott Medway
(74) *Attorney, Agent, or Firm* — Fish & Richardson P.C.

(57) ABSTRACT

A needle shield comprising at least two different plastic materials of different flexibility and a central aperture of variable diameter. The central aperture comprises a first diameter for retaining a needle cap therein. The diameter of the central aperture changes upon removal of the needle cap from the first diameter to a second diameter by virtue of a memory effect of the material of the needle shield. The needle shield is made by an injection molding process.

10 Claims, 2 Drawing Sheets

(56) References Cited

U.S. PATENT DOCUMENTS

| | | | | |
|---|---|---|---|---|
| 5,498,244 | A * | 3/1996 | Eck | 604/198 |
| 5,624,400 | A * | 4/1997 | Firth et al. | 604/110 |
| 5,658,259 | A * | 8/1997 | Pearson et al. | 604/232 |
| 6,004,278 | A * | 12/1999 | Botich et al. | 600/576 |
| 6,004,296 | A | 12/1999 | Jansen et al. | |
| 6,280,421 | B1 * | 8/2001 | Kirchhofer et al. | 604/218 |
| 6,342,045 | B1 * | 1/2002 | Somers | 604/110 |
| 6,648,858 | B2 | 11/2003 | Asbaghi | |
| 6,743,203 | B1 * | 6/2004 | Pickhard | 604/139 |
| 7,097,634 | B2 * | 8/2006 | Gilbert | 604/150 |
| 7,666,168 | B2 * | 2/2010 | Millerd | 604/198 |
| 8,663,129 | B2 * | 3/2014 | Allen et al. | 600/576 |
| 8,821,453 | B2 * | 9/2014 | Doyle et al. | 604/197 |
| 2007/0112310 | A1 * | 5/2007 | Lavi et al. | 604/245 |
| 2009/0105661 | A1 * | 4/2009 | Chevallier et al. | 604/192 |
| 2010/0298770 | A1 * | 11/2010 | Rubinstein et al. | 604/110 |

\* cited by examiner

SAFETY DEVICE FOR A PRE-FILLED SYRINGE AND INJECTION DEVICE

CROSS REFERENCE TO RELATED APPLICATIONS

The present application is a U.S. National Phase Application pursuant to 35 U.S.C. §371 of International Application No. PCT/EP2011/060324 filed Jun. 21, 2011, which claims priority to European Patent Application No. 10168324.1 filed on Jul. 2, 2010. The entire disclosure contents of these applications are herewith incorporated by reference into the present application.

FIELD OF INVENTION

The present invention relates to a needle shield for a safety device and to a safety device that provides needle safety. More particularly, the invention relates to a safety device for pre-filled syringes. The safety device is adapted to avoid accidental needle stick injuries and needle injuries before, during and after an injection of a medication or drug contained in the pre-filled syringe. In particular, the safety device provides needle safety for a subcutaneous self-administrated injection or for an injection administered by a health-care professional. The present invention further relates to injection devices comprising a pre-filled syringe.

BACKGROUND

Pre-filled syringes that are filled with a selected dosage of a medication are well known injection devices for administering the medication to a patient. Safety devices for covering a needle of a pre-filled syringe before and after use are also well known. Typically, these devices comprise a needle shield that is either manually moved or moved by the action of a relaxing spring to surround the needle.

A different type of safety devices known in the state of the art solves the object of providing needle safety by arranging the pre-filled syringe movable relative to a body, wherein the pre-filled syringe is retracted into the body after the injection.

The European Patent Application EP 1 321 158 A1 describes a safety device for a sheathed injection syringe. A needle guard of the safety device has a dilatable opening. A ring is movably arranged around the needle guard and is positionable over the distal portion of the needle guard so as to reconfigure the needle guard and contract the opening.

Document U.S. Pat. No. 4,871,355 discloses a needle and blood collection tube holder with a protective covering to reduce the possibility of accidental needle stick injuries. The tube holder comprises an inner and an outer tube defining a needle protection chamber. A diaphragm is mounted to the forward end of the outer tube. The diaphragm includes individual sections or leafs forming a central orifice of variable diameter adapted expand so that protective sheaths of different sizes may be inserted therein.

SUMMARY

It is an object of the present invention to provide an improved needle shield for a safety device that prevents accidental needle stick injuries.

It is a further object of the present invention to provide an improved safety device for a pre-filled syringe.

It is a further object of the invention to provide an improved injection device comprising a pre-filled syringe that is safe to handle and in particular prevents accidental needle stick injuries.

The object is achieved by a needle shield according to claim 1, a safety device according to claim 6 and by an injection device according to claim 9.

Preferred embodiments of the invention are given in the dependent claims.

In the context of this specification, the terms distal and proximal are defined from the point of view of a person performing an injection. Consequently, a distal direction refers to a direction pointing towards the body of a patient receiving an injection and a distal end defines an end of an element that is directed towards the body of the patient. Respectively, the proximal end of an element or the proximal direction is directed away from the body of a patient receiving the injection and opposite to the distal end or distal direction.

A needle shield for a safety device is made from at least two different plastic materials of different flexibility. The needle shield comprises central aperture of variable diameter. The central aperture comprises a first diameter for retaining a needle cap therein. The diameter of the central aperture changes upon removal of the needle cap from the first diameter to a second diameter by virtue of a memory effect of the material of the needle shield. According to the invention, the needle shield is made by an injection moulding process.

In particular, thermoplastic materials are used to make the needle shield of the safety device. The invention allows an integrated two-component needle shield. Advantageously, high production rates and minimal scrap losses are achievable by the process of injection moulding, so that the safety device can be cost-efficiently mass-produced.

The variable diameter of the central aperture changes to limit an entry-depth of a body part of a person, in particular a finger, may enter into the needle shield through the central aperture. Thus, the needle shield with the variable central aperture provides improved needle safety and prevents accidental needle stick injuries.

Preferably, the variable diameter of the central aperture is provided by a needle shield that is made from different plastics materials of different flexibility, so that the needle shield can be cost-efficiently produced in high quantities.

According to a possible embodiment of the invention, the needle shield is made from an arbitrary combination of plastics material of the following material classes: polymers, elastomers, silicone and silicone elastomer. Alternatively, the needle shield is made from natural rubber. The variable diameter of the central aperture is provided by the material properties of the different plastics materials. Preferably, at least one of the plastics materials provides the needle shield with a shape memory. The plastics materials of the material classes are inexpensive, so that production costs of the needle shield may be reduced.

According to yet another possible embodiment of the invention, at least one of the materials used to make the needle shield has a shape memory. The variable diameter of the central aperture changes from a first diameter to a second diameter by a memory effect of the material of the needle shield. The second diameter is smaller than the first diameter and limits the entry-depth of a body part of a person, in particular a finger, may enter into the needle shield through the central aperture. The needle shield provides a simple means to improve the needle safety by material properties.

Complicated mechanisms that are prone to malfunction are avoided, which in turn allows for a reliable use of the needle shield.

According to yet another possible embodiment of the invention, the needle shield comprises a substantially cylindrical lateral side of the needle shield that is made from a relatively stiff plastics material. This prevents the needle shield from being deformed in a way that causes an unintended re-exposure of the hypodermic needle.

According to yet another possible embodiment of the invention, the lateral side of the needle shield is formed by four substantially planar side walls of the needle shield, wherein adjacent side walls of the needle shield are orthogonal to each other.

According to yet another possible embodiment, a distal end wall of the needle shield is made from a relatively flexible plastics material. The distal end wall comprises the central aperture. The flexible plastics material of the distal end wall is expandable, so that the variable opening of the central aperture is formed.

In an alternative embodiment, the distal end wall comprises a peripheral part and an opening part adjacent to the central aperture. The peripheral part of the distal end wall is made from a relatively stiff plastics material, wherein the opening part of the distal end wall is made from a relatively flexible plastics material. Thus, a variable central aperture is provided, while at the same time the peripheral part of the distal end wall provides the needle shield with a sufficient stiffness and stability, so that accidental needle stick injuries are prevented by the needle shield surrounding the hypodermic needle.

According to the invention, a safety device for a pre-filled syringe comprises a hollow support body to retain the pre-filled syringe therein and a needle shield slidably arranged relative to the support body. The needle shield comprises a central aperture of variable diameter.

The needle shield with the central aperture of variable diameter reduces requirements of other parts of the safety device, in particular requirements to the spatial dimension of the support body that is adapted to retain the pre-filled syringe. Thus, the central aperture with the variable diameters provides a means to reduce production costs for the safety device. The safety device according to the invention can be cost-efficiently mass-produced, which in particular allows for a use of the safety device in combination with disposable pre-filled syringes.

The variable diameter of the needle shield improves the safety features for injection devices that rely on a mechanism that provides needle safety by surrounding a hypodermic needle of the pre-filled syringe with the needle shield, or alternatively, for injection devices that rely on a retraction mechanism, whereby the pre-filled syringe is retracted within the support body after the injection has been performed.

According to a possible embodiment of the invention, the variable diameter of the central aperture changes from the first diameter to the second diameter. The dimensions of the safety device can be adapted to the limited entry-depth. In particular, the requirements for a safe distance, by which a distal tip of the hypodermic needle has to be spaced away from the central aperture of the needle shield, are reduced. This lowers the requirements for other parts of the safety device, like, for example, the axial length of the support body required to provide needle safety or a spring length of a spring arranged to bias the needle shield.

According to another embodiment of the invention, the needle shield is slidable relative to the support body from at least an advanced position to a retracted position, wherein the needle shield protrudes the support body in the advanced position. The needle shield may be made from an opaque plastics material and may be retained in the advanced position prior to use of the safety device. The hypodermic needle of the pre-filled syringe retained within the support body is hidden from the patient's view before the injection by the needle shield in the advanced position. This eases a possible patient's fear of needles. The safety device is thus particularly suited for performing self-administered injections.

Alternatively, the needle shield is made from a transparent plastics material. A healthcare professional that uses the safety device thus can visually confirm the correct placement of the hypodermic needle relative to the skin of the patient even when the hypodermic needle is surrounded by the needle shield.

As the safety device is both suited for self-administered injections and injections carried out by a healthcare professional, the person referred to as the user or the patient may be one and the same person.

The needle shield in the retracted position allows for a penetration of the skin of the patient to dispose a medication contained in the pre-filled syringe.

According to yet another possible embodiment, the safety device comprises a spring that biases the needle shield with respect to the support body in a distal direction. The spring may be provided as a tension spring, compression spring or torsion spring. Further alternative spring means are within the scope of the invention. The needle shield is thus biased towards the advanced position to provide needle safety and/or hide the hypodermic needle of the pre-filled syringe throughout the injection.

An injection device comprises a safety device with a pre-filled syringe retained therein. The hypodermic needle is attached to a distal end of the pre-filled syringe that is covered by a needle cap. The needle cap is frictionally affixed to the distal end of the pre-filled syringe. The needle cap protrudes through the central aperture of the needle shield, whereby the needle shield frictionally engages the needle cap. The injection device comprising the pre-filled syringe and the safety device combines the aforementioned advantages and avoids inadvertent needle sticks before, during and after an injection delivering the medication beneath the skin of patient.

According to a possible embodiment of the invention, the first diameter of the central aperture corresponds to an outer diameter of the needle cap. The needle cap frictionally engages the needle cap, whereby the material of the needle cap is stressed. Upon removal of the needle cap the material of the needle cap relaxes and the central aperture with the reduced second diameter is formed due to a memory effect of the material of the needle shield. As the needle cap provides needle safety prior to use, the needle shield may be initially retained in the retracted position, wherein the needle cap covering the hypodermic needle protrudes through the central aperture of the needle shield. When the needle shield is retained in the retracted position prior to use, the needle cap can be conveniently gripped and removed by a user of the safety device.

The second diameter of the central aperture is sized to allow the hypodermic needle to protrude through the central aperture of the needle shield, so that the hypodermic needle is allowed to penetrate the skin of the patient when the needle shield is in the retracted position.

According to another embodiment of the invention, the needle shield is retained against a biasing force exerted upon the needle shield by the spring in the retracted position. The biasing force is counteracted by the frictional engagement of the needle shield with the needle cap. Upon removal of the needle cap, the spring relaxes to move the needle shield towards the advanced position, whereby the hypodermic needle of the pre-filled syringe is hidden from the view of the patient.

Further scope of applicability of the present invention will become apparent from the detailed description given hereinafter. However, it should be understood that the detailed description and specific examples, while indicating possible embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will be better understood from the detailed description given in the following. The accompanying drawings are given for illustrative purposes only and do not limit the scope of the present invention.

Corresponding parts are marked with the same reference symbols in all figures.

DETAILED DESCRIPTION

Figure 1:
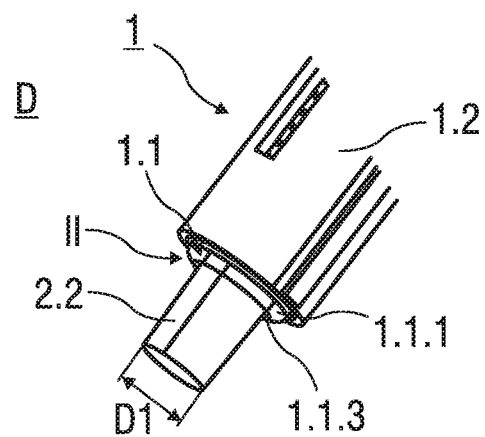
FIG. 1 shows a perspective view of a distal end section of an injection device comprising a pre-filled syringe and a safety device with a needle shield according to a first embodiment, wherein the needle shield comprises a central aperture of variable diameter.
Figure 2:
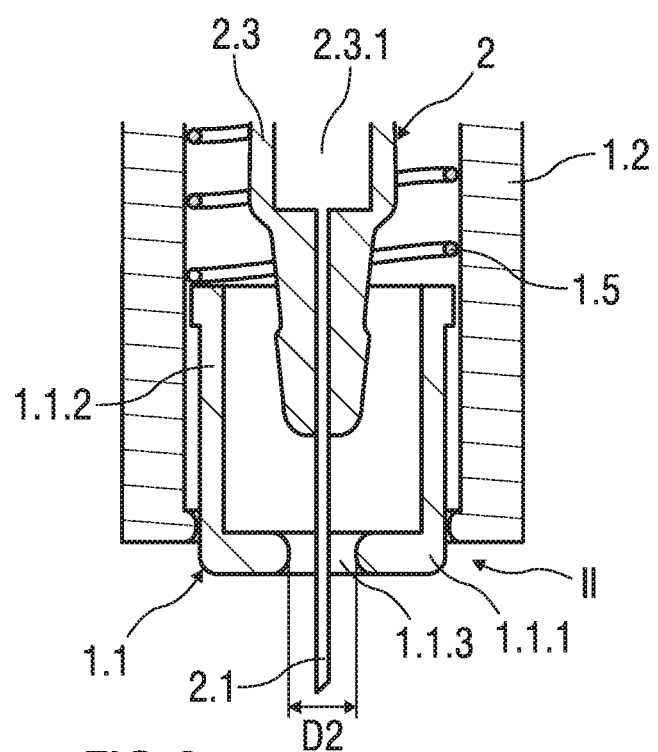
FIG. 2 shows a sectional view of a distal end section of an injection device comprising a pre-filled syringe and a safety device with the needle shield according to the first embodiment, wherein the needle shield comprises a central aperture of variable diameter.
Figure 3:
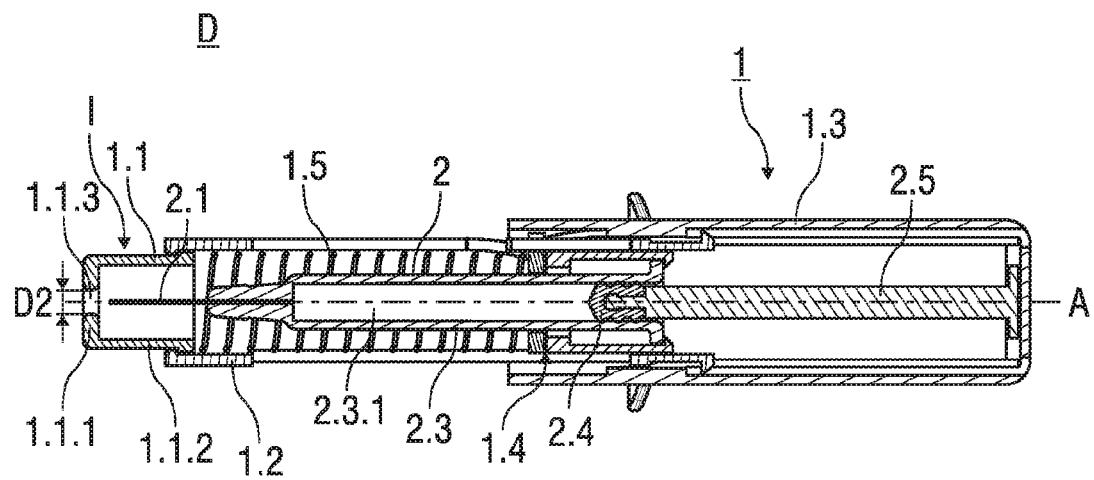
FIG. 3 shows a sectional view of an injection device with the needle shield according to the first embodiment.

FIG. 1 shows a perspective view of a distal end section of an injection device D. FIG. 2 shows the sectional view of the distal end section according to FIG. 1 and FIG. 3 shows a perspective view of the whole injection device D.

The injection device D comprises a safety device 1 and a pre-filled syringe 2 retained within the safety device 1. The safety device 1 comprises a needle shield 1.1 according to a first embodiment of the invention. The injection device D shown in FIGS. 1 and 3 is in a packaged state as it would be presented to an end-user. The needle shield 1.1 is slidable relative to a support body 1.2 between at least one advanced position I and a retracted position II.

With reference to FIG. 1, the needle shield 1.1 is retained in the retracted position II prior to use and substantially received within an open distal end of a tubular support body 1.2 prior to use of the safety device 1.

Alternatively, the needle shield 1.1 may be retained in the advanced position I prior to use. With reference to FIG. 3, the needle shield 1.is shown in the advanced position I after removal of the needle cap 2.2.

Alternatively, the hollow needle shield 1.1 is sized to receive the open distal end of the support body 1.2. In this alternative embodiment, the needle shield 1.1 slides over the support body 1.2 when these parts 1.1, 1.2 are slid relative to each other. Prior to use, a distal end of the support body 1.2 is substantially received within the needle shield 1.1.

As best seen in FIG. 3, the pre-filled syringe 2 retained in the support body 1.2 comprises a hypodermic needle 2.1 that is covered by the needle cap 2.2 prior to use. The pre-filled syringe 2 is retained within the support body 1.2, so that the needle cap 2.2, as illustrated in FIG. 1, protrudes the support body 1.2 in a distal direction and can be easily gripped and manually removed before use of the injection device D.

Additionally, the needle cap 2.2 frictionally engages the needle shield 1.1 to retain the needle shield 1.1 in the retracted position II.

Before the injection is carried out, the needle shield 1.1 is retained in the retracted position II and substantially received within the support body 1.2. The needle shield 1.1 is made from flexible materials, especially from two different plastics materials of different flexibility that may comprise a polymer, an elastomer, silicone and/or a silicone elastomer.

The needle shield 1.1 is made by the process of an injection moulding. The needle shield 1.1 is made from thermoplastic plastics materials.

The needle shield 1.1 of the first embodiment is made from two different plastics materials of different flexibility. The needle shield 1.1 is made by the process of a two shot injection moulding. At least one of the plastics materials being used to form the needle shield 1.1 provides the needle shield 1.1 with a shape memory, so that the needle shield 1.1 is able to return to a pre-determined shape upon stress relief The combination of a relative rigid and a relative flexible material allows the needle shield 1.1 to retain its substantial cylindrical shape whilst being able to stretch over the needle cap 2.2 covering the hypodermic needle 2.1 of the pre-filled syringe 2 prior to use.

Alternatively, the needle shield 1.1 is made from natural rubber.

FIG. 2 shows a sectional view of a distal end section of the support body 1.2 with the needle shield 1.1 retained therein. The needle shield 1.1 comprises a distal end wall 1.1.1 made from a flexible material like an elastomer, silicone or a silicone elastomer. The lateral side 1.1.2 of the substantially cylindrical needle shield 1.1 is made from a relative rigid and stiff plastics material.

Alternatively, the lateral side 1.1.2 is substantially made from a relative flexible material like an elastomer. The lateral side 1.1.2 comprises a plurality of stiffening ribs made from a relative rigid plastics material to provide the needle shield 1.1 with the required stiffness. The stiffening ribs may extend parallel to the central axis A and/or be oriented perpendicular to the central axis A and have the form of circumferential rings moulded into the substantially tubular needle shield 1.1.

The distal end wall 1.1.1 comprises a central aperture 1.1.3 aligned on the central axis A. The central aperture 1.1.3 has a diameter of variable width. In the packaged state shown in FIG. 1, the flexible material of distal end wall 1.1.1 is stretched over the needle cap 2.2 protruding the needle shield 1.1 in the distal direction. The material of the distal end wall 1.1.1 is stressed, so that the central aperture 1.1.3 exhibits a first diameter D1 that corresponds to an outer diameter of the needle cap 2.2.

FIG. 3 shows an example of the injection device D comprising the needle shield 1.1 according to the first embodiment. The injection device D comprises the pre-filled syringe 2 and the safety device 1. The safety device 1 comprises an outer body 1.3 slidably arranged relative to the support body 1.2. The pre-filled syringe 2 comprises a barrel 2.3, the hypodermic needle 2.1 affixed to a distal end of the pre-filled syringe 2, a piston 2.4 and a piston rod 2.5. The hypodermic needle 2.1 is in fluid communication with an inner cavity 2.3.1 of the pre-filled syringe 2 containing a medication. The piston 2.4 provides a fluid-tight seal for a proximal end of the inner cavity 2.3.1. The piston 2.4 is movable in the distal direction by actuating the piston rod 2.5, which in turn can be actuated by moving the outer body 1.3 with respect to the support body 1.2 in the distal direction.

In the example shown in FIG. 3, the pre-filled syringe 2 is affixed to by releasable mounting means 1.4. After an injection has been performed, the mounting means 1.4 is released by the action of a relaxing spring 1.5 arranged within the safety device 1. The spring 1.5 may be provided as a compression spring, a torsion spring or a tension spring. Further alternative kinds of springs are possible. The spring 1.5 biases the needle shield 1.1 with respect to the support body 1.2 in the distal direction.

As indicated in FIG. 1, the needle shield 1.1 is retained in the retracted position II against the biasing force exerted upon the needle shield 1.1 by the frictional engagement of the needle shield 1.1 with the needle cap 2.2.

FIG. 3 illustrates the injection device D after removal of the needle cap 2.2. Upon removal of the needle cap 2.2, the spring 1.5 moves the needle shield 1.1 in the distal direction to the advanced position I, wherein the hypodermic needle 2.1 is surrounded by the needle shield 1.1 in the advanced position I. Furthermore, the flexible material of the distal end wall 1.1.1 expands and unbends upon removal of the needle cap 2.2 as a consequence of the stress relief, so that a central aperture 1.1.3 with a reduced second diameter D2 is formed. The second diameter D2 of the central aperture 1.1.3 is thus established due to a memory effect of the materials being used in the production of the needle shield 1.1.

During the injection, the needle shield 1.1 is moved to the retracted position II, in which the hypodermic needle 2.1 protrudes through the central aperture 1.1.3 with reduced second diameter D2 to dispose a medication beneath the skin of a patient.

Alternatively, the needle shield 1.1 may be retained in the advanced position I prior the injection, wherein the needle shield 1.1 in the advanced position I protrudes the support body 1.2 distally prior to use of the safety device 1.

Additionally or alternatively, the needle shield 1.1 may be releasably retained or permanently locked to the advanced position Ito prevent a re-exposure of the hypodermic needle 2.1.

Figure 4:
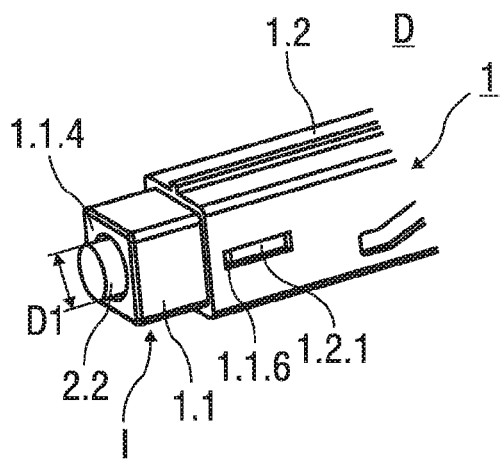
FIG. 4 shows a perspective view of a distal end section of an injection device comprising a pre-filled syringe and a safety device with a needle shield according to a second embodiment, wherein a central aperture of the needle shield has a first diameter.

FIG. 4 shows a safety dev ice 1 for a pre-filled syringe 2 with a needle shield 1.1 according to a second embodiment of the invention. The safety device 1 is in a packaged state as it would be presented to an end-user. The safety device 1 comprises the hollow needle shield 1.1 with a substantially square cross-section.

Alternatively, the needle shield 1.1 may have a substantially rectangular cross-section or be of conventional cylindrical form with a circular cross-section.

Additionally, the needle shield 1.1 may comprise an outwardly protruding flange that rests on the skin of a patient during the injection.

The needle shield 1.1 is received within a hollow support body 1.2 with a substantially square cross-section, wherein the needle shield 1.1 is slidable with respect to the support body 1.2 between an advanced position I and a retracted position II parallel to the central axis A of the safety device 1. Prior to use of the safety device 1, the needle shield 1.1 is retained in the advanced position I, wherein the needle shield 1.1 protrudes the support body 1.2.

Alternatively, the support body 1.2 may comprise a substantially rectangular cross-section.

The injection device D comprises the safety device 1 with the pre- filled syringe 2 retained therein. The pre-filled syringe 2 is retained within the support body 1.2, so that the hypodermic needle 2.1 of the pre-filled syringe 2 protrudes the support body 1.2 in a distal direction. The needle shield 1.1 in the advanced position I surrounds and hides the hypodermic needle 2.1 from the view of the user when the pre-filled syringe 2 is retained within the support body 1.2.

A distal end wall 1.1.1 of the needle shield 1.1 is orientated perpendicular to the lateral side 1.1.2 that is formed by four substantially planar shield side walls. The distal end wall 1.1.1 is designed to rest onto the skin of a patient during the injection and comprises a circular central aperture 1.1.3. The central aperture 1.1.3 has a first diameter Dl corresponding to an outer diameter of a needle cap 2.2 frictionally held on the distal end of the pre-filled syringe 2, wherein the needle cap 2.2 covers the hypodermic needle 2.1 prior to the injection. The needle cap 2.2 distally protrudes beyond the distal end wall 1.1.1, so that the needle cap 2.2 can be manually removed before usage of the safety device 1.

The needle shield 1.1 according to the second embodiment is made from two materials of different flexibility. The lateral side 1.1.2 formed by the planar side walls of the needle shield 1.1 and a peripheral part 1.1.4 of the distal end wall 1.1.1 are made from a relatively stiff plastics material.

Figure 5:
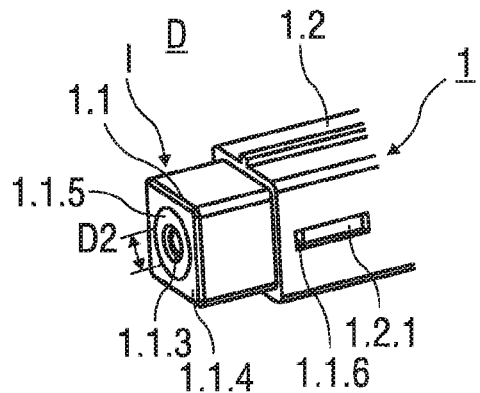
FIG. 5 shows a perspective view of a distal end section of an injection device comprising a pre-filled syringe and a safety device with the needle shield according to the second embodiment, wherein the central aperture of the needle shield has a second diameter.

As best seen in FIGS. 4 and 5, the distal end wall 1.1.1 comprises an opening part 1.1.5 adjacent to the central aperture 1.1.3. The opening part 1.1.5 is made from a flexible and stretchable plastics material like silicone or silicone elastomer. The central aperture 1.1.3 has a variable diameter.

When the needle cap 2.2 is attached to the pre-filled syringe 2 and received inside the central aperture 1.1.3, the opening part 1.1.5 stretches around the needle cap 2.2 to frictionally hold the needle cap 2.2 in the central aperture 1.1.3. After removal of the needle cap 2.2, the flexible material of the opening part 1.1.5 unbends and expands as a consequence of the stress relief resulting in the central aperture 1.1.3 with reduced width and smaller second inner diameter D2. The second inner diameter D2 of the central aperture 1.1.3 is dimensioned to allow the hypodermic needle 2.1 to protrude through the central aperture 1.1.3, whereas a finger of a person is prevented to enter the interior through the central aperture 1.1.3 when the hypodermic needle 2.1 is covered by the needle shield 1.1 to avoid needle stick injuries.

The safety device 1 comprises penetration depth limiting means to limit the penetration depth of the hypodermic needle 2.1 during an intramuscular or subcutaneous injection. The penetration depth limiting means comprise two limiter catches 1.1.6 connected to the needle shield 1.1, wherein each limiter catch 1.1.6 moves within a limiter recess 1.2.1 formed into one side wall of the support body 1.2. The limiter recess 1.2.1 extends along an axial length of the support body 1.2 that corresponds to the penetration depth.

The invention claimed is:

1. A needle shield system comprising
a support body having an interior space;
a needle cap; and
a needle shield operatively connected to the support body such that the needle shield can move between an advanced position and a retracted position, the needle shield comprising a distal end wall and a lateral side, wherein the distal end wall comprises a peripheral part and an opening part, wherein the peripheral part is made from a relatively stiff plastics material, wherein the opening part is made from a relatively flexible plastics material compared to the relatively stiff plastics material, wherein the distal end wall is substantially perpendicular to a longitudinal axis of the support body, wherein the distal end wall comprises a central aperture of variable diameter, wherein the central aperture comprises a first diameter for retaining the needle cap therein, wherein, when the needle cap is retained in the central aperture, the opening part stretches around the needle cap and the peripheral part remains substantially unflexed, wherein the diameter of the central aperture changes upon removal of the needle cap from the first diameter to a second diameter by virtue of a memory effect of the material of the opening part, wherein, when the needle cap is removed from the central aperture, the opening part unbends by virtue of the memory effect and the peripheral part remains substantially unflexed, wherein the needle shield is made by an injection moulding process,
wherein the needle shield is configured to slide into the interior space of the support body and is biased by a spring with respect to the support body in a distal direction.

2. A needle shield system according to claim 1, wherein the needle shield is made from an arbitrary combination of plastics materials of the following classes: polymer, elastomer, silicone and silicone elastomer.

3. A needle shield system according to claim 1, wherein a distal end wall of the needle shield is made from a relatively flexible plastics material.

4. A safety device for a pre-filled syringe comprising: a needle shield system according to claim 1, wherein the needle shield is slidably arranged relative to the support body.

5. A safety device according to claim 4, wherein the needle shield is slidable relative to the support body from at least the advanced position to the retracted position, wherein the needle shield protrudes the support body in the advanced position.

6. An injection device comprising a safety device according to claim 4 and a pre-filled syringe with a hypodermic needle attached to a distal end of the pre-filled syringe, wherein the hypodermic needle is covered by a needle cap frictionally affixed to the distal end of the pre-filled syringe,
wherein the needle cap protrudes through the central aperture of the needle shield, whereby the needle shield frictionally engages the needle cap.

7. An injection device according to claim 6, wherein the first diameter of the central aperture corresponds to an outer diameter of the needle cap.

8. An injection device according to claim 6, wherein the second diameter of the central aperture is sized to allow the hypodermic needle to protrude through the central aperture of the needle shield.

9. An injection device according to claim 6, wherein the needle shield is retained against a biasing force exerted upon the needle shield by a spring in the retracted position by the frictional engagement of the needle shield with the needle cap.

10. A needle shield system comprising:
a support body;
a needle cap;
a biasing element operatively biased to the support body; and
a needle shield biased by the biasing element relative to the support body such that the needle shield can move between an advanced position and a retracted position while being coupled to the support body, the needle shield comprising a distal end wall and a lateral side, wherein the distal end wall is substantially perpendicular to the lateral side, wherein the distal end wall comprises a peripheral part and an opening part, wherein the opening part is made from a relatively flexible plastics material compared to the relatively stiff plastics material, wherein the peripheral part and the opening part are concentrically arranged about a longitudinal axis of the support body, wherein the distal end wall comprises a central aperture of variable diameter, wherein, when the needle cap is retained in the central aperture, the central aperture has a first diameter, the opening part stretches around the needle cap and the peripheral part remains substantially unflexed, wherein when the needle cap is removed from the central aperture, the opening part unbends and the peripheral part remains substantially unflexed and the first diameter of the central aperture changes to a second diameter by virtue of a memory effect of the material of the opening part, wherein the needle shield is made by an injection moulding process, wherein the lateral side of the needle shield is made from a relatively stiff plastics material, whereas the distal end wall is made from a relatively flexible plastics material.

* * * * *